United States Patent [19]
Buxton

[11] Patent Number: 5,147,285
[45] Date of Patent: Sep. 15, 1992

[54] MOVABLE THUMB BRACE

[76] Inventor: Aldene H. Buxton, c/o 416 Fourth St., Warsaw, Ohio 43844-0416

[21] Appl. No.: 738,899

[22] Filed: Aug. 1, 1991

[51] Int. Cl.$^5$ .............................................. A61F 5/00
[52] U.S. Cl. ........................................ 602/22; 602/16
[58] Field of Search ............... 128/26, 77, 87 A, 87 R, 128/88; D24/190

[56] References Cited

U.S. PATENT DOCUMENTS

| | | | |
|---|---|---|---|
| 3,631,542 | 1/1972 | Potter | 128/77 |
| 4,740,126 | 4/1988 | Richter | 623/64 |
| 4,881,275 | 11/1989 | Cazares et al. | 272/67 |

FOREIGN PATENT DOCUMENTS 3026839  2/1982  Fed. Rep. of Germany ... 128/87 A Primary Examiner—Richard J. Apley
Assistant Examiner—Susan L. Weinhoffer
Attorney, Agent, or Firm—Biebel & French

[57] ABSTRACT

A movable thumb brace is provided preferably having a plurality of hinged sections. The tip section has a relatively rigid casing having an upper surface portion and a tip portion. The tip portion includes an outer liner and an inner liner with the outer liner having a cover. The outer liner and the cover extend downwardly along the tip portion. The outer liner extends downwardly beyond the cover and then curves upwardly to its distal end. The inner liner extends downwardly adjacent the outer liner and has a distal end located between the outer liner distal end and the cover. The tip section also has a thumb surface portion which is secured to the tip portion. Adjacent to the tip section is section having a casing for placement adjacent the upper surface of a thumb with this section having an upper surface portion and sidewall portions. The thumb brace of this invention also has a support brace secured to the sidewalls of the section adjacent the tip section with the support brace also being secured to the upper surface portion of the tip section. The thumb brace also includes a palm brace which is secured to the section adjacent the tip section and a thumb guard which is hingedly secured to both the tip section and the section adjacent to it as well as to the support brace. The thumb brace is secured to the body by a wrist strap.

15 Claims, 4 Drawing Sheets

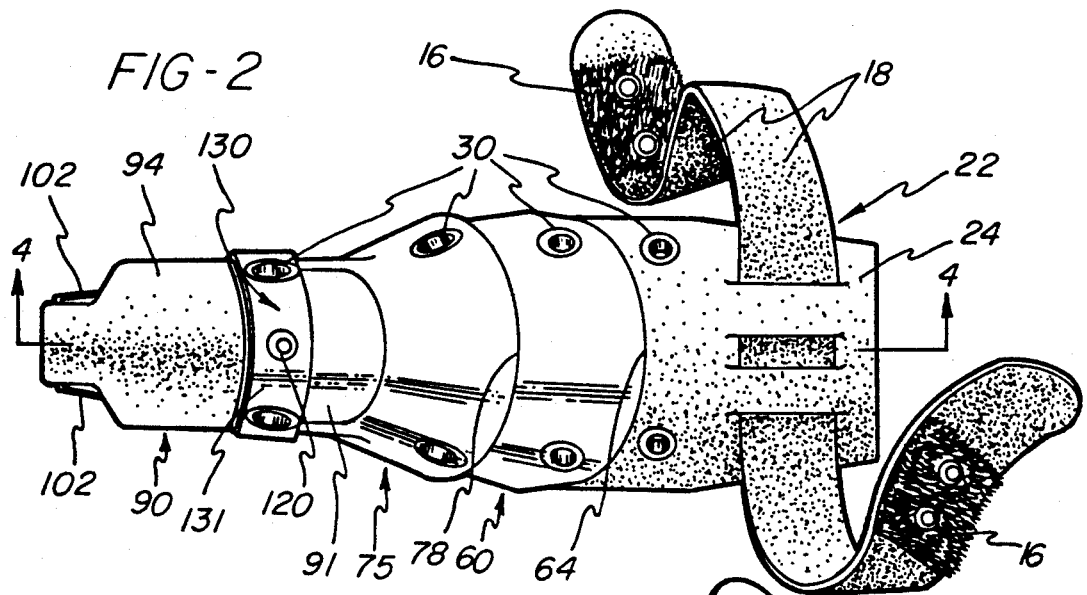
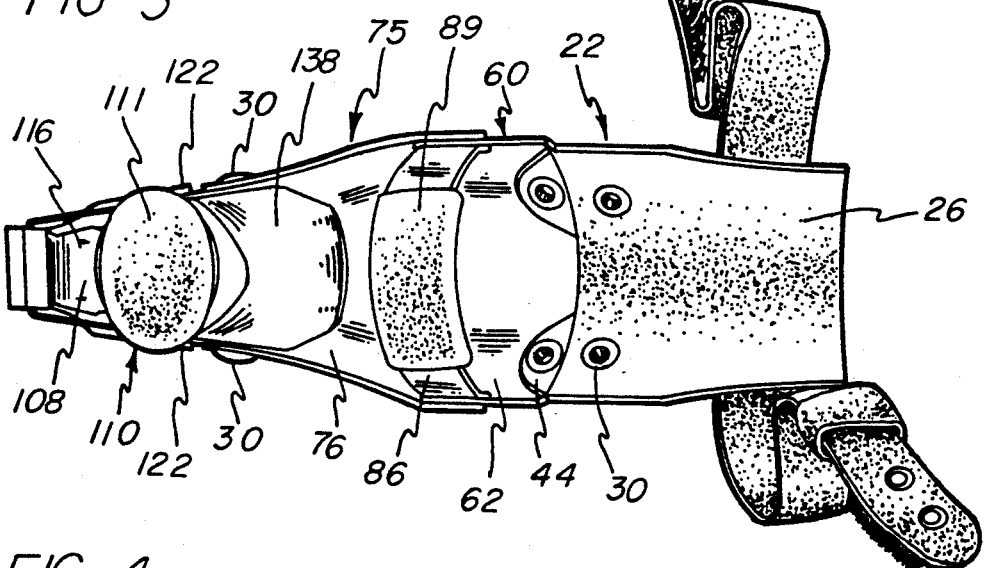
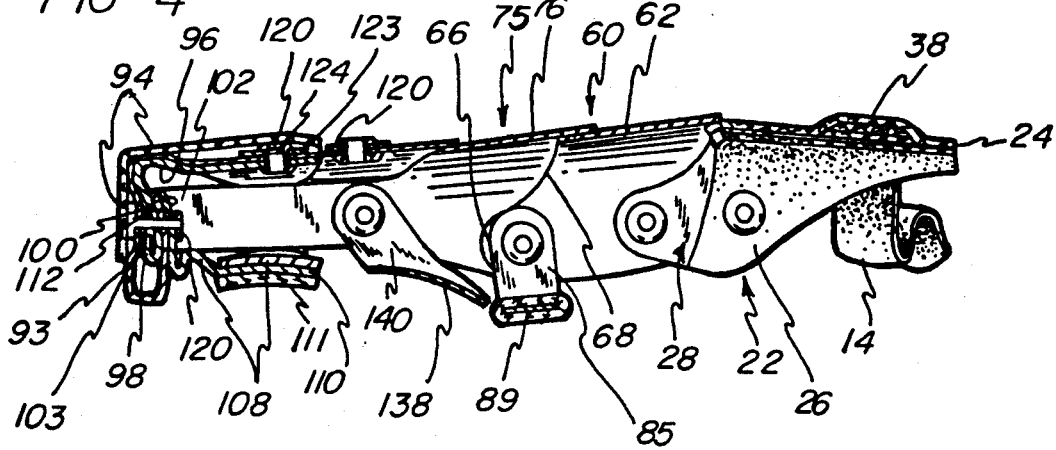

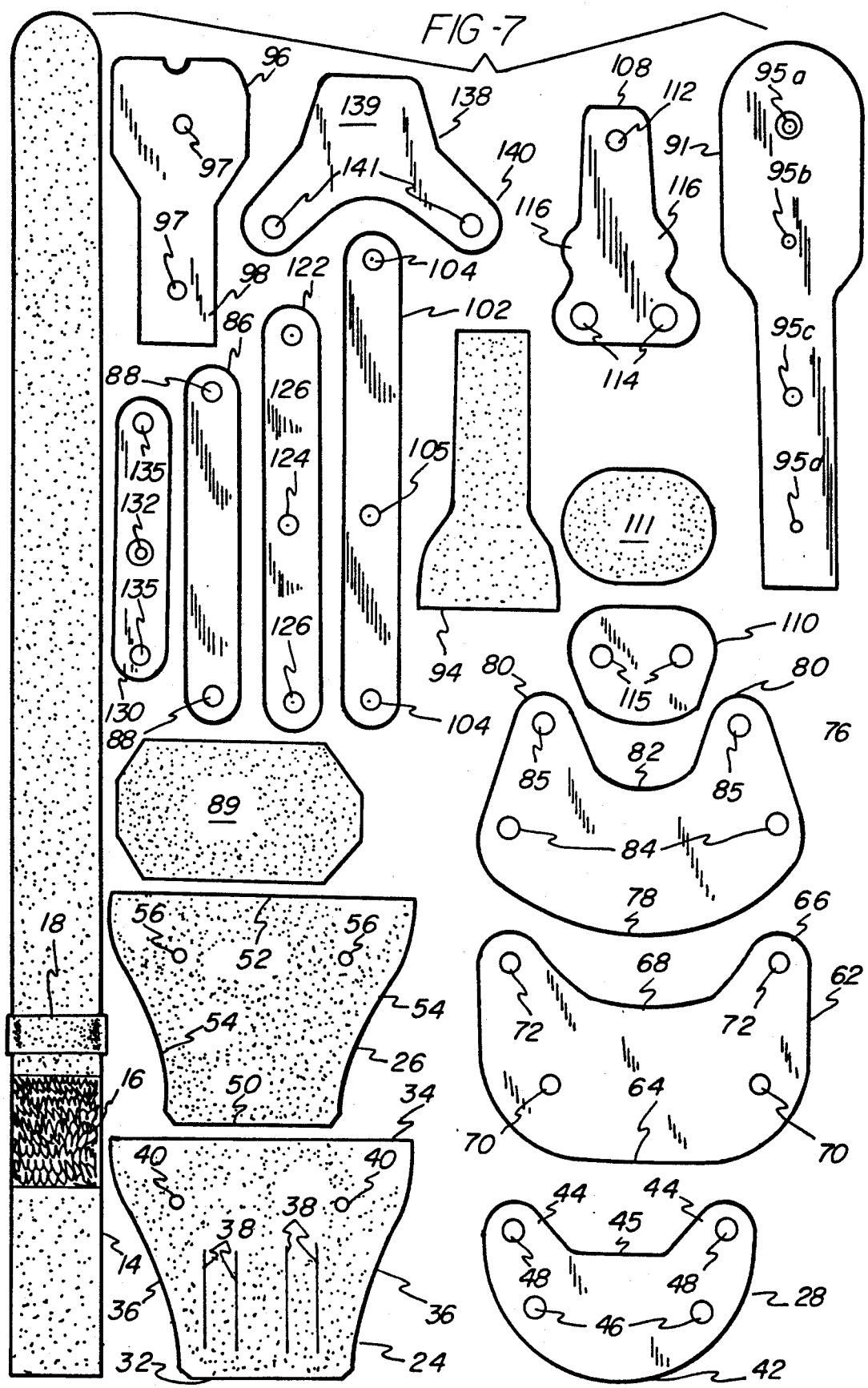

MOVABLE THUMB BRACE

BACKGROUND OF THE INVENTION

The present invention relates generally to thumb braces and the like, and more particularly, to such a device including hinged members incorporated thereinto.

The thumb is particularly important in the grasping and holding of objects. These objects can be relatively heavy such as weighty machine parts, as well as relatively light such as writing instruments. The importance of the thumb in the performing of a variety of tasks cannot be overemphasized.

Occasionally the thumb is subjected to injury such as crushing in a machine, or by accidental severing of the thumb tip necessitating the removal of part of the thumb structure. The removal of a portion of the thumb, particularly the end portion thereof, sometimes is also accompanied by the deterioration of the thumb joint. This deterioration can prevent an individual from being able to grasp even the lightest of objects due to the excruciating pain involved.

Until now a variety of alternative remedies have been proposed for this condition. One potential remedy has been the amputation of the entire thumb and its replacement with a prosthetic device. Another potential remedy has been through the providing of a fairly rigid unbendable cover for the thumb to prevent any nerve sensitive portions of the thumb from coming into direct contact with objects to be grasped. The advantage of this remedy is that amputation and its attendant risks are avoided. The disadvantage associated with this remedy is that, while the thumb is not subjected to pain, the thumb is rendered essentially useless for purposes associated with the mobility of the thumb.

It is thus apparent that the need exists for an improved thumb brace or the like which provides the necessary protection for a damaged thumb as well as providing a desired degree of mobility.

SUMMARY OF THE INVENTION

The problems associated with the prior braces for the thumb are overcome in accordance with the present invention by forming a movable thumb brace comprising a plurality of hinged sections. Portions of these hinged sections are preferably relatively rigid and thus form a protective casing for the thumb. One of the sections comprising an upper surface portion and sidewall portions with the section adjacent this section having an upper surface portion and a tip portion as well as having a thumb surface portion. A support brace is secured to the sidewalls of the former section and to the upper surface portion of the latter section.

The tip portion preferably comprises an outer liner and an inner liner. The outer liner has a cover which along with the outer liner extends downwardly along the tip portion. The outer liner also extends downwardly beyond the cover, yet then curves upwardly to the outer liner distal end. The inner liner extends downwardly adjacent the outer liner and also has a distal end located between the outer liner distal end and the outer liner cover.

The thumb brace also preferably includes a thumb guard hingedly secured to both the support brace and to the tip section, as well as to the section adjacent to said tip section. The thumb surface portion is preferably also secured to the tip portion. Additionally, the thumb brace also preferably includes both a palm brace which is secured to the section adjacent the tip section, and a wrist strap.

The thumb brace also comprises a circumferential brace located as part of the tip section and secured to both the inner and outer liners, preferably at the upper surface portion of the tip section. The circumferential brace is also secured to the thumb surface portion of the thumb brace.

It is the primary object of the present invention to provide a movable thumb brace which may be easily formed, yet which provides adequate protection for the thumb as well as providing the desired mobility.

It is another object of the present invention to provide a thumb brace which may be easily secured about the thumb as well as easily removed.

Still another objective of the present invention is to provide a thumb brace which is relatively light in weight and possessing adequate ventilation so as to be comfortable to wear. Still another objective of the present invention is to provide a thumb brace capable of duplicating many of the tasks associated with healthy thumbs, and more particularly associated with the finger tip and fingernail portions of the thumb.

Other objects and advantages of the invention will be apparent from the following description, the accompanying drawings and the appended claims.

BRIEF DESCRIPTION OF THE DRAWINGS

FIG. 2 is a top elevational view of the thumb brace.

FIG. 3 is a bottom elevational view of the thumb brace.

FIG. 4 is a vertical sectional view taken along line 4—4 of FIG. 2.

FIG. 7 is a top view of the various parts of the thumb brace of this invention, to provide a clearer understanding of the geometric configurations associated with the various components.

DETAILED DESCRIPTION OF THE INVENTION

Figure 1:
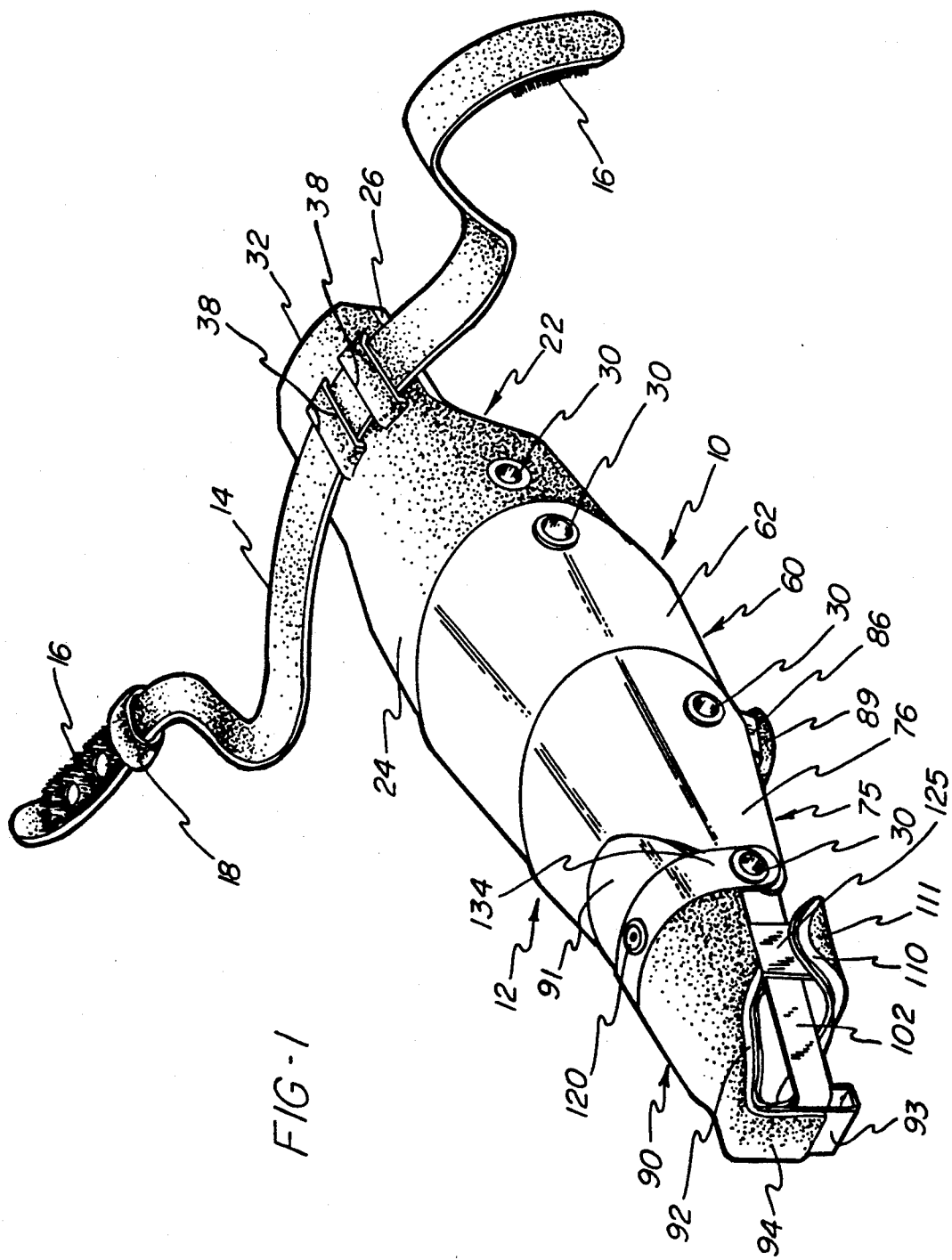
FIG. 1 is a perspective view of a thumb brace in accordance with the present invention.
Figure 6:
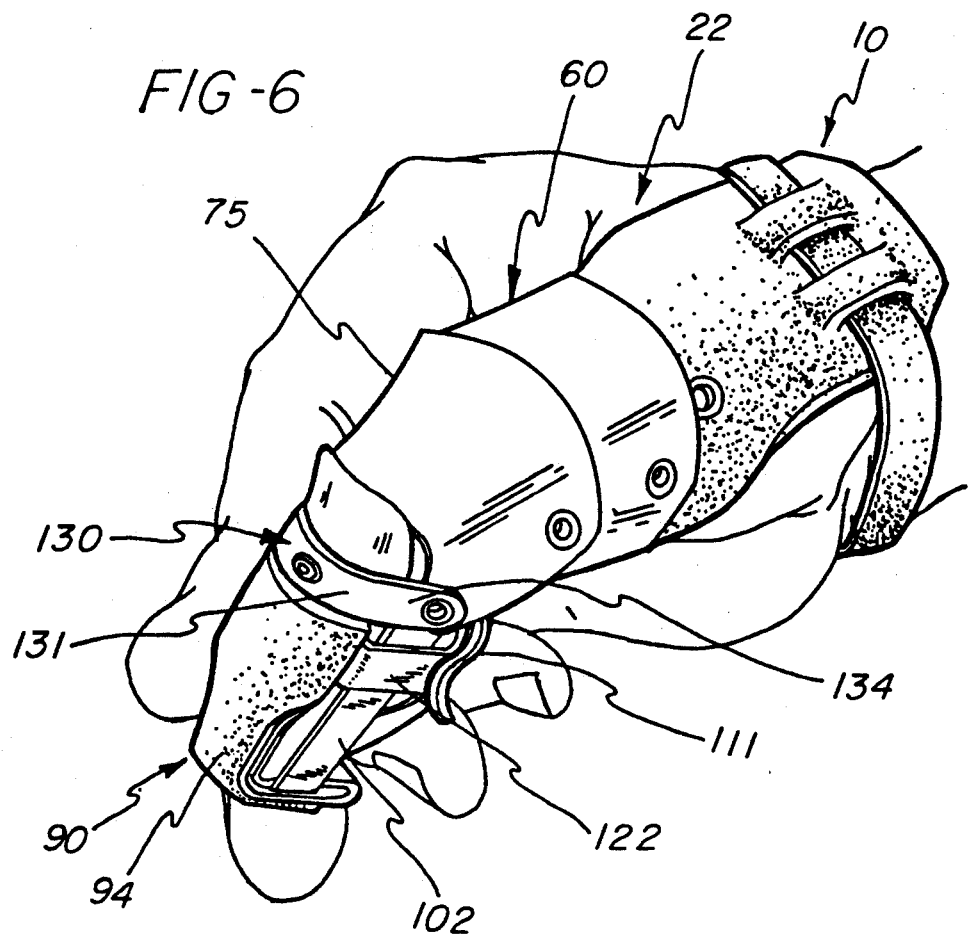
FIG. 6 is a perspective view showing the thumb brace of this invention in operative relationship to a human hand.

FIG. 1 is a perspective view of a movable thumb brace designated generally by the numeral 10. The thumb brace 10 made in accordance with the present invention comprises a thumb enclosure 12 in the form of a segmented casing having a wrist strap 14 secured near one end of the somewhat longitudinally formed thumb brace 10. The thumb brace comprises a relatively rigid casing for placement adjacent the upper surface of a thumb with the casing having an upper surface portion as well as sidewall portions. Much of the lower surface of the thumb brace is open such that these open portions along with the smaller open portions along the sidewall of the casing near the tip portion and the openings provided when the thumb brace is bent as shown in FIG. 6 assist in providing ventilation for the enclosed thumb.

The wrist strap 14 functions as a means for retaining the thumb brace securely about the thumb of an individual. As can be seen in the drawing figures, the wrist strap 14 includes strap fastening means 16, preferably in the form of coordinating VELCRO ® patches or snaps. Additionally, to assist in the alignment of the wrist strap and to present a more aesthetic appearance, a loop 18 is provided on one portion of the wrist strap for passage therethrough of the end most portion of the opposite end of the wrist strap.

As can be seen best in a comparison of FIGS. 1, 2, 3, 4 and 6, the thumb brace 10 is comprised of a number of segmented sections. The first or proximal section 22 is secured to the wrist strap 14. This first section 22 includes a flexible top cover 24 and flexible bottom cover 26, preferably formed of leather or a soft plastic. Sandwiched between top cover 24 and bottom cover 26 is a first plate 28 with the top cover 24, bottom cover 26, and first plate 28 being held together by eyelets 30.

The top cover visible in FIGS. 1 and 2 is also shown in FIG. 7 as having a top cover proximal edge 32, a top cover distal edge 34, and a pair of top cover tapered sidewalls 36. The top cover 24 is shown as having two pairs of slits 38 formed longitudinally in top cover 24. These pairs of slits 38 are shown in FIGS. 1, 2, 4, 5 and 6 as permitting the passage therethrough a portion of the wrist strap 14. The top cover also includes top cover apertures 40 located intermediate the slits 38 and the distal edge 34 with each one of the top cover apertures 40 being located closer to the top cover tapered sidewalls 36 than to each other.

FIG. 7 in addition to showing the geometric configuration associated with top cover 24 also shows the geometric configuration associated with first plate 28. Wrist plate 28 can be appreciated as having a curved proximal edge 42, with its ends extending to rounded first plate distal corners 44. There is also a first plate distal edge 45 which in the assembled embodiment of the invention runs perpendicular to the longitudinal axis of the thumb brace. The first plate 28 has a first set of first plate apertures 46 located near the proximal end of the plate. There is also a second set of first plate apertures 48 formed in the rounded first plate distal corners 44. As can be seen in FIG. 7 the bottom cover 26 also includes a proximal edge 50 and a distal edge 52 along with tapered sidewalls 54 and a pair of bottom cover apertures 56 located near the bottom cover distal edge 52.

Proximal or first section 22 is secured by eyelets 30 through the second set of first plate apertures to the second section of the thumb brace of the invention. The second section 60 has as its primary component a second plate 62 shown in FIGS. 1, 2 and 7. Second plate 62 has a slightly curved proximal edge 64 with rounded second plate distal corners 66. As opposed to the relatively straight first plate distal edge 45, the second plate has a slightly rounded distal edge 68. A first set of second plate aperture 70 are formed relatively near the slightly curved distal edge 64, while one each of a second set of second plate apertures 72 are formed in each of the rounded second plate distal corner 66.

The second plate 62 is secured by eyelets 30 to the third section 75 of this thumb brace 10. One of the main components of the third section 75 is a third plate 76. This third plate is shown in FIGS. 1, 2, 4 and 7 as having a curved proximal edge 78. The third plate also has rounded third plate distal corners 80. A relatively short curved distal edge 82 extends between the rounded third plate distal corners 80. A first set of third plate apertures 84 are located relatively near to the curved proximal edge 78 while one each of a second set of third plate apertures 85 are found in each of the rounded third plate distal corners 80.

Figure 5:
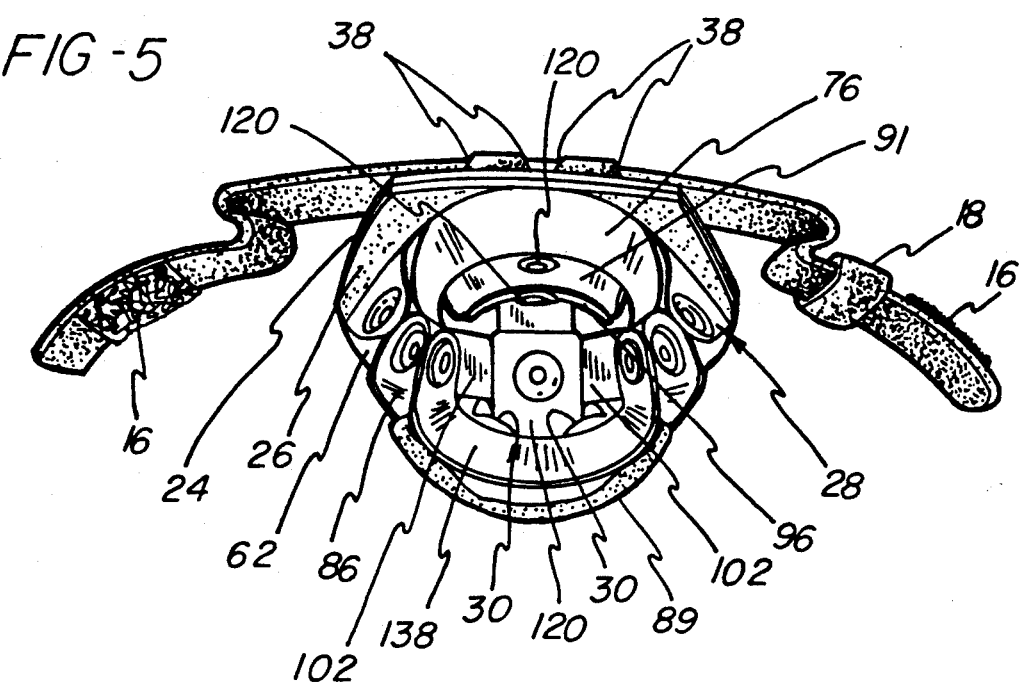
FIG. 5 is a rear elevational view taken from the rear of FIG. 1.

Also secured at the same eyelet 30 as holds the second plate 62 and third plate 76 to one another is a palm brace 86. The palm brace extends transversely with respect to the longitudinal axis of the thumb brace 10. The palm brace 86 is shown in FIGS. 1, 3, 4, 5 and 7 with FIG. 7 showing the palm brace apertures 88 formed at the opposite ends of the strip 86. The palm brace in its operative embodiment as best shown in FIGS. 3, 4 and 5 is bent or curved so as to be secured to the second and third plates 62, 76 and pass beneath the central longitudinal axis associated with the thumb brace.

The palm brace 86 is pivotable about eyelets 30 and has its lowermost surface enclosed in a palm brace cover 89 as can best be seen in FIGS. 3 and 4. The palm brace cover 89 initially is configured as shown in FIG. 7 but is then wrapped about palm brace 86 to prevent the brace from riding up on the palm beyond the base of the thumb of the user.

A fourth or distal section 90 of thumb brace 10 is comprised of a fourth plate 91. As can be seen in FIGS. 1 and 2, only a portion of the fourth plate 91 is actually visible when compared to the entire configuration of the fourth plate 91 shown in FIG. 7. Fourth plate 91 has a fourth plate section 92 as well as a tip cover 93 which is formed relatively perpendicularly thereto and depends downwardly from the upper surface portion of the movable thumb brace 10. Overlapping most of the fourth plate 91 is fourth plate cover 94 which is substantially co-extensive thereto. This fourth plate cover 94 is also preferably formed from a leather or other soft plastic.

As can best be seen in FIGS. 4 and 7, the fourth plate has formed therein fourth plate apertures 95a, 95b, 95c and 95d. This fourth plate 91 acts much as an outer liner. Meanwhile secured adjacent the fourth plate or outer liner 91 is a fourth plate inner liner 96. The fourth plate inner liner 96 is shown in FIG. 7 as being formed with a pair of apertures 97 located along the longitudinal axis of the fourth plate inner liner 96. The inner liner 96 has a liner distal end 98. As can best be seen in FIG. 4, the inner liner extends along the upper surface of the thumb brace and thence downwardly adjacent the outer liner until near the bottom of the tip cover 93. The outer liner extends beyond the lowermost portion of the fourth plate cover 94 and in fact curves upwardly to the tip distal end 100 located inwardly from the outer surface of the fourth plate. The inner liner has a distal end 98 which is located between the outer liner distal end 100 and the cover 94 and, as seen in FIG. 4, curves outwardly and upwardly toward the cover.

The tip section, or fourth section, 90 also comprises a sidewall plate 102. As can be seen in comparing FIGS. 4, 5 and 7, the fourth section sidewall plate 102 has a tip surface portion 103 which extends parallel to tip cover 93. Additionally, the sidewall plate has a pair of sidewall plate apertures 104 through which an eyelet 30 passes for securing of sidewall plate 102 to the plate adjacent the tip section, namely third plate 76 of third section 75. Further, a tip surface portion aperture 105 is provided in the portion of the sidewall plate 102 which when formed comprises part of the tip surface portion 103.

The fourth section 90 also comprises a fourth section bottom section 108. Having a thumb surface plate 110 coextensive with the thumb surface plate 110 is a thumb surface cover 111, preferably formed of leather or other pliable material. The bottom section 108 in a comparison of FIGS. 3, 4 and 7 has a bottom aperture 112 formed in the portion of the bottom section means to secure the tip portion of the bottom section 108 to both the inner liner 96 as well as the outer liner 91.

The bottom section also has thumb surface apertures 114 at the rounded corners opposite the bottom section tip aperture 112. These bottom section thumb surface apertures 114 are oriented so as to correspond with thumb surface plate apertures 115 of the thumb surface plate 110. The fourth section bottom section 108 as can be seen in FIG. 7 has two bottom section tapered portions 116 which are gently rounded. These portions as can be seen in FIG. 3 extend upwardly from the remainder of the bottom section and terminate just inwardly of the sidewall plate 102.

A number of rivets 120 are associated with the fourth section 90. For example, a rivet 120 can be seen in FIG. 4 as passing through and holding together the inner and outer liners, the tip surface portion 103 of the sidewall plate 102 and the bottom section tip aperture 112 of the bottom section 108. Another rivet, as can be seen in a comparison of FIGS. 4 and 5, passes through the inner and outer liner portions associated with the upper surface of the thumb brace and secure those components to the circumferential brace 122, with this brace best being seen in FIGS. 1 and 6.

The circumferential brace 122 as is also shown in FIG. 7 comprises a top surface 123, which top surface is adjacent the fourth plate cover 94. The circumferential brace also has a top aperture 124 through which rivet 120 passes. Additionally, there are a pair of opposed side surfaces 125 having near their ends circumferential brace end apertures 126. These circumferential brace end apertures are aligned with the thumb surface plate apertures 115 to permit the passage therethrough of eyelets 30.

In comparing FIGS. 1, 2 and 6 it will be appreciated that a support brace 130 is also provided as a part of this invention. This support brace 130 is shown in FIG. 7 as being a relatively short oblong shape. The support brace 130 has a support brace top portion 131, as can be appreciated from FIG. 2, and a support brace top portion aperture 132, as can be appreciated from FIG. 7, through which a rivet 120 fits in the operative embodiment of the invention, as can be appreciated from FIG. 1. The support brace 130 also is formed so that in the operative embodiment there are a pair of support brace side portions 134 as can be appreciated from FIG. 1, with each support brace side portion 134 having formed therein a support brace side portion aperture 135 as shown in FIG. 7. Eyelets 30 pass through the support brace side portion apertures 135 and secure the support brace to the third plate 76, to the fourth section sidewall plate 102 and to a thumb guard 138. The thumb guard is hingedly secured to both the tip section and the section adjacent the tip section, as well as to the support brace 130.

As can be seen in FIGS. 3, 4, 5 and 7, thumb guard 138 is formed having a central portion 139 and a pair of winged end portions 140. Each winged end portion 140 has formed therein end portion apertures 141 such that when the thumb guard is secured to this invention the winged end portions curve upwardly and are secured inwardly of the sidewall plate 102 by eyelet 30 as discussed above. As can be appreciated in FIGS. 3 and 4, the portion of the thumb guard closest to the palm brace 86 curves slightly downwardly to facilitate the passage thereon of a human thumb when it is inserted into the thumb brace disclosed by this invention.

The components of this invention are formed of a relatively rigid material, preferably 22 gauge stainless steel, with the exception being the various leather or plastic covers or straps discussed above. The eyelets 30 are preferably double telescoping eyelets, although it could be possible to also utilize pop rivets provided adequate hinge motion is retained. As is best shown in FIG. 6, when installed in operative embodiment on a thumb, the thumb brace 10 of this invention has its wrist strap 14 secured about the wrist and the thumb inserted forwardly into the thumb brace as shown. Preferably the thumb brace is formed such that the longitudinal dimensions of the various sections cooperate with the various lengths associated with the thumb of the wearer to provide a comfortable fit. When worn, the various covers 94 and 111 provide a surface which has enough friction to permit those portions of the thumb brace to function similarly to human skin. The lowermost portion of the outer liner as shown best in FIGS. 1 and 4 permits additional dexterity similar to that possible through the use of a human fingernail.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. A movable thumb brace comprising
   first and second hinged components, said first component being a tip component comprising a relatively rigid casing having an upper surface portion and a tip portion, said first component also having a thumb surface portion, said second component being adjacent said first component and comprising a relatively rigid casing for placement adjacent the upper surface of a thumb, said relatively rigid casing having an upper surface portion and side wall portions,
   a support brace secured to said tip component upper surface portion and to said second component side walls,
   a thumb guard hingedly secured by one hinge to both said first and second components, and to said support brace, and
   a wrist strap.

2. The thumb brace according to claim 1 wherein said tip portion comprises an outer liner, an inner liner, and a cover, said outer liner and said cover extending downwardly along said tip portion, said outer liner extending downwardly beyond said cover and then curving upwardly to the distal end of said outer liner, said inner liner extending downwardly adjacent said outer liner, and said inner liner having a distal end located between said outer liner distal end and said cover.

3. The thumb brace according to claim 2 wherein said thumb surface portion is secured to said upper surface portion of said tip component.

4. The thumb brace according to claim 2 which includes a palm brace secured to said second component.

5. The thumb brace according to claim 2 wherein said tip component comprises a sidewall plate, said sidewall plate secured to said second component and to both said outer liner and inner liner.

6. The thumb brace according to claim 2 wherein said tip component comprises a circumferential brace, said circumferential brace secured to both said outer liner and said inner liner at said tip component upper surface portion, and said circumferential brace also secured to said thumb surface portion.

7. A movable thumb brace comprising first and second hinged components, said first component being a tip component comprising a tip portion, said tip portion comprising an outer liner, an inner liner, and a cover, said outer liner having a cover, said outer liner and said cover extending downwardly along said tip portion, said outer liner extending downwardly beyond said cover and then curving upwardly to the distal end of said outer liner, said inner liner extending downwardly adjacent said outer liner and said inner liner having a distal end located between said outer liner distal end and said cover, said second component comprising a casing for placement adjacent the upper surface of a thumb, and a support brace secured to said first component and to said second component.

8. The thumb brace according to claim 7 wherein said first component comprises a thumb surface portion.

9. The thumb brace according to claim 7 wherein said thumb brace comprises a wrist strap.

10. The thumb brace according to claim 7 which includes a thumb guard hingedly secured by one hinge to both said first and second components, and to said support brace.

11. The thumb brace according to claim 7 wherein said thumb surface portion is secured to said upper surface portion of said tip component.

12. The thumb brace according to claim 7 which includes a palm brace secured to said tip component.

13. The thumb brace according to claim 7 wherein said tip component comprises a sidewall plate, said sidewall plate secured to said second component and to both said outer liner and inner liner.

14. The thumb brace according to claim 7 wherein said tip component comprises a circumferential brace, said circumferential brace secured to both said outer liner and said inner liner at said tip component upper surface portion, and said circumferential brace also secured to said thumb surface portion.

15. A movable thumb brace comprising first and second hinged components, said first component being a tip component comprising a relatively rigid casing having an upper surface portion and a tip portion, said tip portion comprising an outer liner, an inner liner, and a cover, said outer liner and said cover extending downwardly along said tip portion, said outer liner extending downwardly beyond said cover and then curving upwardly to the distal end of said outer liner, said inner liner extending downwardly adjacent said outer liner and said inner liner having a distal end located between said outer liner distal end and said cover, said tip component also having a thumb surface portion, said thumb surface portion secured to said upper surface portion of said tip component, said second component comprising a relatively rigid casing for placement adjacent the upper surface of a thumb, said relatively rigid casing having an upper surface portion and side wall portions, a support brace secured to said first component upper surface portion and to said second component side walls, a palm brace secured to said tip component, a thumb guard hingedly secured by one hinge to both said tip and second components, and to said support brace, and a wrist strap.

* * * * *